United States Patent
Dlaikan-Campos

(10) Patent No.: US 11,992,426 B2
(45) Date of Patent: May 28, 2024

(54) STENT FOR SPLINTING A VEIN, AND SYSTEM FOR PUTTING IN PLACE A STENT

(71) Applicant: MaRVis Interventional GmbH, Krün (DE)

(72) Inventor: Nasib Dlaikan-Campos, Würselen (DE)

(73) Assignee: MARVIS INTERVENTIONAL GMBH, Krün (DE)

( * ) Notice: Subject to any disclaimer, the term of this patent is extended or adjusted under 35 U.S.C. 154(b) by 122 days.

(21) Appl. No.: 17/213,358

(22) Filed: Mar. 26, 2021

(65) Prior Publication Data

US 2021/0212849 A1 Jul. 15, 2021

Related U.S. Application Data

(62) Division of application No. 15/520,582, filed as application No. PCT/EP2015/074155 on Oct. 19, 2015, now Pat. No. 11,291,567.

(30) Foreign Application Priority Data

Oct. 21, 2014 (DE) ..................... 10 2014 115 337.5

(51) Int. Cl.
*A61F 2/90* (2013.01)
*A61F 2/95* (2013.01)
(Continued)

(52) U.S. Cl.
CPC .................. *A61F 2/90* (2013.01); *A61F 2/95* (2013.01); *D04C 1/06* (2013.01);
(Continued)

(58) Field of Classification Search
CPC .... A61F 2/2439; A61F 2/2418; A61F 2/2436; A61F 2/9661; A61F 2/9662; A61F 2/966; A61F 2220/0083; A61B 2017/00243
See application file for complete search history.

(56) References Cited

U.S. PATENT DOCUMENTS

| 5,725,547 A | 3/1998 | Chuter |
| 5,873,906 A | 2/1999 | Lau et al. |

(Continued)

FOREIGN PATENT DOCUMENTS

| DE | 19750971 | 7/1999 |
| DE | 19843822 | 3/2000 |

(Continued)

OTHER PUBLICATIONS

Search Report of the European Patent Office, dated May 7, 2021, for European Patent Application EP 21151615.8. German. 8 pages.
(Continued)

*Primary Examiner* — Kelly J Bekker
*Assistant Examiner* — Andrew P. Restaino
(74) *Attorney, Agent, or Firm* — HoustonHogle LLP

(57) ABSTRACT

The invention relates to a stent and a system for putting in place a stent. Said stent is used especially for splinting a vein and consists of a braided, tubular supporting member (2) that has a minimum length of 60 mm. The supporting member is braided from one or more wires in such a way that portions of the wire or wires, resp., delimit rhombuses. The disclosed stent is characterized in that in the unloaded state of the stent, the longitudinal size of most of the rhombuses (7) in the longitudinal direction (15) of the stent (1) is not shorter than the transversal size of the rhombuses.

2 Claims, 8 Drawing Sheets

Figures 1A, 1B:
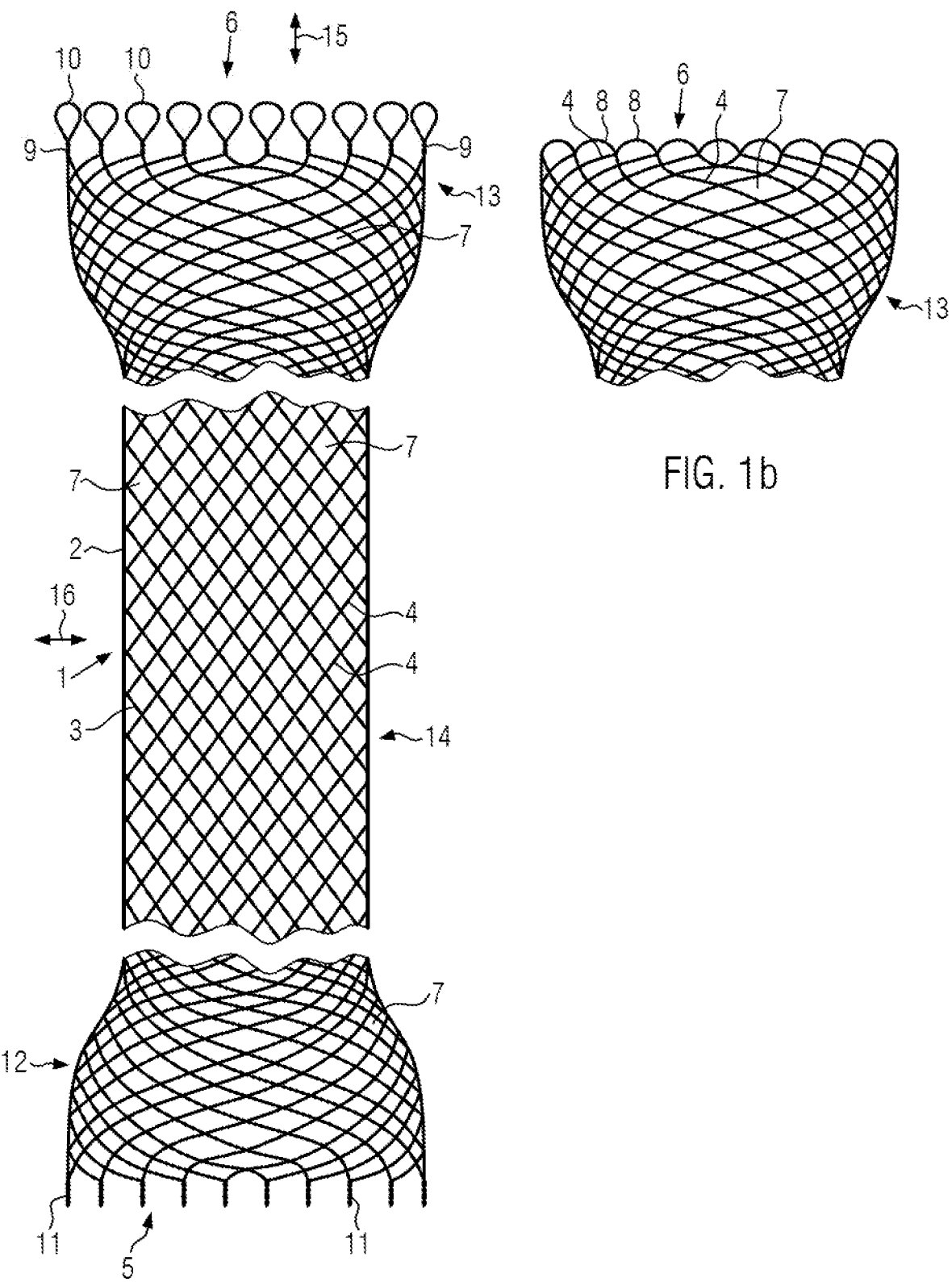

(51) Int. Cl.
*D04C 1/06* (2006.01)
*A61F 2/966* (2013.01)

(52) U.S. Cl.
CPC ..... *A61F 2002/9511* (2013.01); *A61F 2/9661* (2020.05); *D10B 2509/06* (2013.01)

(56) References Cited

U.S. PATENT DOCUMENTS

| | | | |
|---|---|---|---|
| 6,083,257 | A | 7/2000 | Taylor et al. |
| 7,097,653 | B2 | 8/2006 | Freudenthal et al. |
| 8,979,918 | B2 | 3/2015 | Murayama |
| 2003/0135265 | A1 | 7/2003 | Stinson |
| 2004/0138734 | A1 | 7/2004 | Chobotov et al. |
| 2005/0119722 | A1 | 6/2005 | Styrc et al. |
| 2005/0143809 | A1 | 6/2005 | Salahieh et al. |
| 2006/0155363 | A1* | 7/2006 | LaDuca ............ A61F 2/06 623/1.16 |
| 2007/0100427 | A1 | 5/2007 | Perouse |
| 2007/0112415 | A1 | 5/2007 | Bartlett |
| 2007/0293932 | A1 | 12/2007 | Zilla et al. |
| 2009/0099640 | A1* | 4/2009 | Weng ............ A61F 2/95 623/1.11 |
| 2009/0264985 | A1 | 10/2009 | Bruszewski |
| 2010/0256732 | A1 | 10/2010 | Shin et al. |
| 2010/0262157 | A1 | 10/2010 | Silver et al. |
| 2011/0060398 | A1 | 3/2011 | Tupil et al. |
| 2011/0082490 | A1 | 4/2011 | Connelly et al. |
| 2012/0083871 | A1 | 4/2012 | Ryan |
| 2012/0221093 | A1 | 8/2012 | McHugo |
| 2013/0006347 | A1 | 1/2013 | McHugo |
| 2013/0090720 | A1 | 4/2013 | Mahr et al. |
| 2014/0277560 | A1 | 9/2014 | Walak |
| 2014/0277573 | A1 | 9/2014 | Gill et al. |
| 2014/0343670 | A1* | 11/2014 | Bakis ............ A61F 2/2436 623/2.11 |
| 2016/0206452 | A1 | 7/2016 | Berez et al. |
| 2019/0083228 | A1 | 3/2019 | Dickinson et al. |

FOREIGN PATENT DOCUMENTS

| | | |
|---|---|---|
| DE | 102007061931 | 6/2009 |
| EP | 2 165 684 | 3/2010 |
| WO | WO 9625124 | 8/1996 |
| WO | WO 2003065934 | 8/2003 |
| WO | WO 2006037086 | 4/2006 |
| WO | WO 2009126244 | 10/2009 |

OTHER PUBLICATIONS

International Preliminary Report on Patentability, dated Apr. 25, 2017, from International Application No. PCT/EP2015/074155, filed Oct. 19, 2015. English and German. 28 pages.

Search Report of the German Patent Office, dated Jun. 26, 2015, for German priority application DE 10 2014 15337.5, filed on Oct. 21, 2014. German. 12 pages.

International Search Report and Written Opinion of the International Searching Authority, dated Apr. 21, 2016, from International Application No. PCT/EP2015/074155, filed Oct. 19, 2015. English: Search Report only; German 9 pages.

Tanaka, N., et al., "Conformity of Carotid Stents with Vascular Anatomy: Evaluation in Carotid Models," Am. J. Neuroradiol. 25, 604-607 (2004).

* cited by examiner

| Ø Draht $D_D$ | Ø Stent $D_S$ | Faktor F | n (Stränge) rechnerisch | n (Stränge) tatsächlich |
|---|---|---|---|---|
| 0,05 | 10 | 59,6 | 29,8 | 28 bis 32 |
| 0,05 | 12 | 59,6 | 35,8 | 32 bis 36 |
| 0,05 | 14 | 59,6 | 41,7 | 40 bis 44 |
| 0,05 | 16 | 59,6 | 47,7 | 44 bis 48 |
| 0,05 | 18 | 59,6 | 53,6 | 52 bis 56 |
| 0,05 | 20 | 59,6 | 59,6 | 56 bis 60 |
| 0,08 | 10 | 33,8 | 27,0 | 24 bis 28 |
| 0,08 | 12 | 33,8 | 32,4 | 32 bis 36 |
| 0,08 | 14 | 33,8 | 37,9 | 36 bis 40 |
| 0,08 | 16 | 33,8 | 43,3 | 40 bis 44 |
| 0,08 | 18 | 33,8 | 48,7 | 48 bis 52 |
| 0,08 | 20 | 33,8 | 54,1 | 52 bis 56 |
| 0,10 | 10 | 25,0 | 25,0 | 24 bis 28 |
| 0,10 | 12 | 25,0 | 30,0 | 28 bis 32 |
| 0,10 | 14 | 25,0 | 35,0 | 32 bis 36 |
| 0,10 | 16 | 25,0 | 40,0 | 36 bis 40 |
| 0,10 | 18 | 25,0 | 45,0 | 40 bis 44 |
| 0,10 | 20 | 25,0 | 50,0 | 48 bis 52 |
| 0,12 | 10 | 19,2 | 23,0 | 20 bis 24 |
| 0,12 | 12 | 19,2 | 27,6 | 24 bis 28 |
| 0,12 | 14 | 19,2 | 32,3 | 28 bis 32 |
| 0,12 | 16 | 19,2 | 36,9 | 32 bis 36 |
| 0,12 | 18 | 19,2 | 41,5 | 40 bis 44 |
| 0,12 | 20 | 19,2 | 46,1 | 44 bis 48 |
| 0,15 | 10 | 13,4 | 20,1 | 20 bis 24 |
| 0,15 | 12 | 13,4 | 24,1 | 24 bis 28 |
| 0,15 | 14 | 13,4 | 28,1 | 28 bis 32 |
| 0,15 | 16 | 13,4 | 32,2 | 32 bis 36 |
| 0,15 | 18 | 13,4 | 36,2 | 36 bis 40 |
| 0,15 | 20 | 13,4 | 40,2 | 40 bis 44 |
| 0,18 | 10 | 9,4 | 16,9 | 16 bis 20 |
| 0,18 | 12 | 9,4 | 20,3 | 20 bis 24 |
| 0,18 | 14 | 9,4 | 23,7 | 24 bis 28 |
| 0,18 | 16 | 9,4 | 27,1 | 24 bis 28 |
| 0,18 | 18 | 9,4 | 30,5 | 28 bis 32 |
| 0,18 | 20 | 9,4 | 33,8 | 32 bis 36 |
| 0,20 | 10 | 7,6 | 15,2 | 16 bis 20 |
| 0,20 | 12 | 7,6 | 18,2 | 20 bis 24 |
| 0,20 | 14 | 7,6 | 21,3 | 20 bis 24 |
| 0,20 | 16 | 7,6 | 24,3 | 24 bis 28 |
| 0,20 | 18 | 7,6 | 27,4 | 28 bis 32 |
| 0,20 | 20 | 7,6 | 30,4 | 32 bis 36 |
| 0,22 | 10 | 6,0 | 13,2 | 12 bis 16 |
| 0,22 | 12 | 6,0 | 15,8 | 16 bis 20 |
| 0,22 | 14 | 6,0 | 18,5 | 20 bis 24 |
| 0,22 | 16 | 6,0 | 21,1 | 20 bis 24 |
| 0,22 | 18 | 6,0 | 23,8 | 24 bis 28 |
| 0,22 | 20 | 6,0 | 26,4 | 24 bis 28 |
| 0,25 | 10 | 4,4 | 11,0 | n.a. |
| 0,25 | 12 | 4,4 | 13,2 | 12 bis 16 |
| 0,25 | 14 | 4,4 | 15,4 | 16 bis 20 |
| 0,25 | 16 | 4,4 | 17,6 | 16 bis 20 |
| 0,25 | 18 | 4,4 | 19,8 | 20 bis 24 |
| 0,25 | 20 | 4,4 | 22,0 | 20 bis 24 |
| 0,30 | 10 | 2,4 | 7,2 | n.a. |
| 0,30 | 12 | 2,4 | 8,6 | n.a. |
| 0,30 | 14 | 2,4 | 10,1 | n.a. |
| 0,30 | 16 | 2,4 | 11,5 | n.a. |
| 0,30 | 18 | 2,4 | 13,0 | 12 bis 16 |
| 0,30 | 20 | 2,4 | 14,4 | 16 bis 20 |
| 0,35 | 10 | 1,6 | 5,6 | n.a. |
| 0,35 | 12 | 1,6 | 6,7 | n.a. |
| 0,35 | 14 | 1,6 | 7,8 | n.a. |
| 0,35 | 16 | 1,6 | 9,0 | n.a. |
| 0,35 | 18 | 1,6 | 10,1 | n.a. |
| 0,35 | 20 | 1,6 | 11,2 | 12 |

FIG. 6

STENT FOR SPLINTING A VEIN, AND SYSTEM FOR PUTTING IN PLACE A STENT

RELATED APPLICATIONS

This application is a Divisional of U.S. patent application Ser. No. 15/520,582, filed on Apr. 20, 2017, which is a § 371 National Phase Application of International Application No. PCT/EP2015/074155, filed on Oct. 19, 2015, which claims priority to German Application No. 10 2014 115 337.5, filed on Oct. 21, 2014, all of which are incorporated herein by reference in their entirety.

The present invention relates to a stent for splinting a vein, and a system for putting in place a stent.

It is known to use stents which serve to maintain patency of the vessels in case of vessel stenosis and occlusions. Stents are mainly applied in arteries. Such a stent is a short tubular part which is made from metal or plastic. Commonly it possesses a lattice-like structure which is obtained by (laser) cutting of a tubular semi-finished material.

Meanwhile stents for veins are also available, in particular for veins in the region of the legs. For such venous stents the requirements, however, are significantly different from those for common stents, in particular arterial stents. Veins do not have the stiffness of arteries, are much thinner-walled, and, therefore, "softer" and more flexible. Consequently, venous stents must be appropriately adapted in their stiffness to the requirements for splinting of such a soft venous wall. On the other hand, splinting of a vein must be possible over much longer distances as in an artery, and the venous stent, on the one hand, should be elastic enough so that it can optimally align to the vein and, on the other hand, it does not impair movement of the vein and its structure in the body.

A venous stent of the company Boston Scientific is known under the name Wallstent® Venous Endoprothesis. It is provided as a lattice which is wire-braided. This stent is available in lengths of 20 mm to 90 mm with diameters of 10, 12, 14 and 16 mm in various combinations of the two dimensions. The individual stents are cut to the respective length from a long, braided wire tube. Thus at the ends of the stents sharp wire ends protrude and the individual wires are freely movable against each other so that both ends of the braid are not stably fixed but can easily deform.

Tanaka et al. (Conformity of Carotid Stents with Vascular Anatomy: Evaluation in Carotid Models; Am J Neuroradiol 25, 604-607 (2004)) report the problem that the conformity between the self-expanding Wallstent and the vascular anatomy is limited. Due to the lack of flexibility vessel curvatures are erected and straightened in an undesired manner. As a result stent-induced bends of the further winding course of the vein may occur.

Furthermore, the company Cook Medical distributes a stent with the name Cook Zilver Vena Stent which is implanted in veins. This stent is manufactured by laser cutting of a metal tube and is available in lengths of 60, 100 and 140 mm with diameters of 14 or 16 mm, resp. The radial force of this laser-cut stent is higher than that of the typical arterial stents but not optimally sufficient for splinting of veins. In addition, the stent shows the typical effect of laser-cut stents when bent, i.e. that the individual struts at the inner side of the bend protrude into the hollow cavity and, thereby, into the bloodstream so that an increased risk of thrombogenicity results, and at the outer side of the bend they press into the vessel wall which leads to lesions and stronger injuries. The venous stents always are in move with the blood vessel, especially if the venous stent has to be positioned in the region of a joint or e.g. the hip.

The company Optimed as of late offers the Optimed sinus-Venous Stent as a venous stent. This stent is available in lengths of 60 to 150 mm, each with diameters of 12, 14, 16 and 18 mm. This is a laser-cut stent, too, which is manufactured from a metal tube by cutting out the struts which have a very elaborate and complex pattern. The flexibility of this stent has been improved as compared to the Cook Zilver Vena Stent by ring-type systems of struts which are independent of each other and which in turn are interconnected to each other by so-called "flash-link" struts.

The company Veniti Medical recently has received the CE mark for its newly developed Veniti Vici Venous Stent System. Here, too, these are laser-cut stents. These stents are available in lengths of 60, 90 and 120 mm and each with diameters of 12, 14 and 16 mm. The strut design is different from that of the other two venous stents from Cook and Optimed. Just the same as with the Optimed product, the more complex strut design shall allow an improved radial force and flexibility.

The general disadvantages of laser-cut stents which, as a result of their design and by matter of principle, always tend to take the shape of the metal tube from which they are manufactured are amongst others a) a limited opening force (radial force), b) a limited flexibility and long-term loading capability at the junctions of the struts with each other (therefrom resulting a risk of breakage of the struts and, thereby, the stents), and c) as a consequence a high effort to obtain stents which to some extent may reasonably well attach to the venous vessel wall. As venous stents have to move e.g. along with the movements of joints, and the wall of the vein can easily collapse due to its thin and weak effectuation, a high risk of migration of the venous stent from the original position and, therefore, an endangerment of the patient exist. The radial force of laser-cut stents, in addition, by design and manufacturing is rather limited so that a very high effort in the design of the stent struts is necessary to achieve an improved radial force. For a laser-cut stent the combination of the necessary radial force with the required flexibility and the optimal coverage of the vessel wall is achievable only with a very complex stent design, but so far only to a limited extent. Strut designs developed for arterial stents are more or less inappropriate for venous stents as these have to fulfil other requirements.

The requirements applying to venous stents for several technical and medical parameters consequently are much higher than for arterial stents. This is the reason for the very limited number of known dedicated venous stents as compared to the very large number of known arterial stents. Furthermore, except for the Wallstent® which has not been explicitly developed as a venous stent, no braided venous stent is known. Venous stents need to have a larger diameter as not only the general patency of the vessel but also the achieved diameter which can be maintained open is of high medical relevance in order to secure the normal pressure in distal venous vessels.

Braided endovascular stents (i.e. arterial stents) which are known in the state of the art provide the following characteristics:

| Property | Advantage | Disadvantage |
| --- | --- | --- |
| low number of crossing points or round ends, resp. | quick and cost-efficient manufacturing (in particular when manually braided) | low stability of the braid, potentially incision into the tissue or the vessel wall |
| wide/wide-drawn rhombuses ("transverse") | increase of the radial force | high elongation low stability of braid |
| low density of the braid | improved compressibility | limited usability, |
| shorter versions (none longer than 100 mm) and small diameters (none above 20 mm) | quick and cost-efficient manufacturing (also when manually braided) | for longer distances several implants must be positioned connected in series, associated with all related operative and medical problems |

Internal tests have demonstrated that non-optimized stents mostly have a too high elongation of the stent and an insufficient radial force (opening force). Therefore, these stents frequently attach to the vessel wall only in parts and are not sufficiently effective in soft vessels. Unsplinted regions remaining laterally next to the stent braids hold a substantial risk of embolization because blood continuously flows through the braid.

Braided stents are known e.g. from DE 198 43 822 A1, US 2009/0264985 A1, WO 2009/126244 A2, DE 197 50 971 A1 and WO 03/065934 A2.

U.S. Pat. No. 5,873,906 A shows a foldable catheter which in the folded state is held together by a sack knot. The sack knot has two ends whereas the knot can be untied by pulling at one end of the sack knot.

US 2004/0138734 A1 describes an implant with self-expanding elements. These self-expanding elements are held together for insertion of the implant by loop-shaped belts, whereas the belts themselves are held together by release wires which extend through the loops of the belts. Once the release wires are pulled out of the loops then the belts disengage and the self-expanding elements can expand.

US 2007/0100427 A1 discloses an apparatus with which a stent can be refolded when released to the blood vessel. For that a rod-shaped support is permanently affixed to the stent in which filaments for contraction of the stent are guided.

US 2012/0221093 A discloses a catheter system for positioning of a stent with which a stent is held at both its ends and during positioning in the blood vessel is held under tension.

US 2010/262157 A discloses another system for positioning of a stent in which the stent is inserted in compressed state into a catheter by a guiding rod. The stent is secured by a thread which then is pulled out. The stent for positioning in the blood vessel freely sits in the catheter and at the desired position is pushed out of the catheter with another pushing rod. A change of the position of the stent in the blood vessel is not possible anymore after pushing it out of the catheter.

Another system for positioning of a stent is disclosed in US 2013/0006347 A. The system provides an inner and an outer catheter whereas threads are affixed at the inner and the outer catheter so that they can touch the stent at both ends and put it under tension.

U.S. Pat. No. 7,097,653 discloses an apparatus for positioning of an implant whereas the implant is actively stretched during positioning.

The object of the invention is to create a stent for splinting of a vein with which an optimal splinting of veins is possible, and a system for putting in place a stent.

This object is achieved by a system for positioning of a stent with the features of the claims.

A stent for splinting of a vein according to the invention consists of a braided tubular supporting member. The stent preferably has a length of at least 60 mm. The supporting member is braided from one or more wires in such a manner that sections of the wire or the wires, resp., delimit rhombuses.

According to a first aspect of the present invention a venous stent is characterized in that it provides one or more reinforcement sections in which the rhombuses are shorter in longitudinal direction than the rhombuses in the other sections of the stent.

The rhombuses of the reinforcement sections can, but must not be longer in transversal direction than the rhombuses of the other sections. The reinforcement sections can be provided with the same diameter as the other sections. In this case the strands in the region of the reinforcement sections during manufacturing of the stent are braided with a greater braiding angle relative to the longitudinal extension of the stent than in the other sections. The reinforcement sections may also have a greater diameter than the other sections of the stent. In this case the reinforcement section may also be manufactured in the same way as the above described widened regions by squeezing together or compression of the respective section.

Independent of how many reinforcement sections are provided such a stent has particularly special and advantageous mechanical properties. The reinforcement sections provide the stent with a high radial stiffness. The other sections located between the reinforcement sections, whose rhombuses have a greater longitudinal extension than the rhombuses of the reinforcement sections, are, however, softer and more flexible. Thereby they provide a high flexibility or suppleness to the stent. These other sections, therefore, in the following are called hinge sections. The alternating arrangement of reinforcement and hinge sections hence creates a type of link chain built from the stiff, ring-shaped reinforcement sections and the more flexible hinge regions. Hereby such a venous stent can adapt to any curves of the vein. At the same time the reinforcement sections prevent that the vein can collapse.

Altogether the structure of such a stent according to the invention with alternating reinforcement sections and hinge sections provides a high stability to and prevents a high elongation of the hinge sections. The reinforcement sections block an interaction of the individual hinge sections with each other so that the resulting elongation essentially results as the sum of the elongation of the individual hinge regions. Elongation of the individual hinge sections is reduced by that the rhombuses of the hinge region neighboring the respective reinforcement section are less movable than those in a continuous braid with the rhombus structure of a hinge section. Hence, the sum of the elongation of the individual hinge sections is lower than the elongation of a continuous braid with the rhombus structure of a hinge region which in its length is identical to the sum of the lengths of the individual hinge regions.

Preferably the stent has at least two and in particular at least three reinforcement sections, whereas between two neighboring reinforcement sections a hinge section is arranged.

As the stent consists of a braided tubular supporting member it does not possess branches. The series of alternating reinforcement sections and hinge sections thus is provided in a non-branched stent.

The length of the reinforcement sections preferably is smaller than the length of the hinge regions.

The length of the reinforcement sections may be less than or equal to 48 rhombuses, 42 rhombuses, 36 rhombuses, 30 rhombuses, 24 rhombuses, 21 rhombuses, 18 rhombuses, 15 rhombuses, twelve rhombuses, ten rhombuses, nine rhombuses, eight rhombuses, seven rhombuses, six rhombuses, or five rhombuses in longitudinal direction.

The length of the reinforcement sections comprises preferably at least two rhombuses, three rhombuses, four rhombuses, five rhombuses, or ten rhombuses in longitudinal direction of the stent.

The length of the hinge region can be greater than or equal to six rhombuses, nine rhombuses, ten rhombuses, eleven rhombuses, twelve rhombuses, 15 rhombuses, 18 rhombuses, 21 rhombuses, 24 rhombuses, 30 rhombuses, 36 rhombuses, 42 rhombuses, 48 rhombuses, 54 rhombuses, or 60 rhombuses in longitudinal direction.

Preferably the rhombuses of the one or more reinforcement sections in unloaded state of the stent are at least 10%, in particular at least 15%, or at least 30%, resp., shorter than the rhombuses of the other sections of the stent.

Particularly for the unloaded state of the stent it applies that the stent provides one or more reinforcement sections in which the rhombuses in longitudinal direction are shorter than the rhombuses of the other sections of the stent. In the customary loaded state in a vein the rhombuses of the reinforcement sections remain shorter than the rhombuses of the other sections. However, it is possible to squeeze the stent together in such a way that the reinforcement sections elongate such that this relationship remains no longer valid.

As the stent is braided from continuous strands which extend from the distal to the proximal end it has a homogeneous braid structure in the respect that the stent in the region of a random cross section has the same number of strands. The stent thus possesses in axial direction a high tear resistance which is much higher than for comparable stents which are cut from a tube. For such stents the struts in flexible sections are very thin and due to the cutting from a tube section they do not possess a homogeneous material structure which is much more tear resistant. Furthermore, wires during manufacturing are strain-hardened which provides a very high tear resistance to them. The hinge sections of the venous stent according to the invention thereby are much more stable than corresponding flexible sections of a stent cut from a tube section.

Such a venous stent can have one, two or more reinforcement sections. In particular it may be appropriate to provide reinforcement sections in periodic distances of e.g. 2 to 5 cm. For a stent with a length of 10 to 30 cm thus five to 20 reinforcement section may be provided.

According to another aspect of the present invention the stent is characterized by that in unloaded state the longitudinal extension of most of the rhombuses in longitudinal direction of the stent is not shorter than the transversal extension of the rhombuses. This especially applies for the rhombuses of the above described hinge regions.

According to the invention thus at least 60% or 70%, resp., of the rhombuses, in particular 80%, and preferably 90% of the rhombuses are provided with a longitudinal extension which in unloaded state is not shorter and preferably even longer than the transversal extension.

The following findings form the basis of the invention:

Veins are a low pressure system. They have thin vessel walls and, therefore, are very soft and easily collapsible. Consequently they do not have such a straight orientation as arteries but rather frequently have numerous curves and bendings. Veins have a higher proportion of connective tissue and a lower proportion of muscle tissue than arteries. Due to this thinner stabilizing muscle layer of the vein, completely different mechanical requirements result for venous stents than for arterial stents, which necessitates a different product design. For achievement of a sufficient stabilization of venous obstructions (stenosis) accordingly for venous stents a significantly higher radial force and concurrently a higher flexibility is necessary as compared to arterial stents. If the stent does not optimally attach to the vessel wall the risk exists that it dislocates due to the rather strong movement of the veins (particularly in the limbs), i.e. may dislocate away from the original position in an uncontrolled manner.

With the stent according to the invention, the disadvantages of laser-cut stents, which particularly realize when using them for splinting veins, as well as the disadvantages of a simple, only cut-to-length braided stent which does not provide any special adaptation for the intended application, are overcome.

An ideal venous stent shall have a great length, a sufficiently high radial force, and a radial force distribution as consistent as possible from the one to the other end. The high radial force must be maintained over the entire life of the patient. It must be flexible, achieve a high wall conclusiveness, and must not show a tendency for contraction after insertion. Furthermore, it must be easily deployable.

Known braided stents possess rhombuses whose transversal extension is greater than their longitudinal extension. The rhombuses hence are extended in transversal orientation. Such a shape of the rhombuses provides high compression stability to the stent by which the vessels can be correspondingly strongly supported. The inventors of the present invention, however, have realized that during compression of such a stent it is very strongly elongated, which means that a small reduction of the diameter by compression of the stent leads to a strong elongation of the stent. If the rhombuses, however, are extended in longitudinal direction then the elongation of the stent during compression is much lower. Rhombuses extended in longitudinal direction lead to a reduced compression stability than with rhombuses extended in transversal direction.

As the vessel walls of veins are rather soft as compared to those of arteries a high compression stability and concurrently a high flexibility is necessary for venous stents. It has turned out that the reduction of the compression stability can be sufficiently compensated by providing a high number of strands and use of an appropriately adapted wire diameter. Herewith it is possible to create a venous stent which is optimally adapted to the stability of the vessel walls of veins. Using longitudinally extended rhombuses, such an adaptation can be made very precisely without significantly impairing other properties of the stent.

Venous stents differentiate from arterial stents in that they are significantly longer. Arterial stents mostly have a length of a few centimeters. Venous stents are applied for splinting of veins over a longer section which is at least 6 cm, and usually even significantly longer, i.e. at least 10 cm, in particular at least 15 cm, or at least 20 cm, or at least 25 cm, resp. If one compresses such long braided venous stents then the compression of the stent inevitably leads to a distinct up to strong elongation of the stent. The inventors have realized that with longitudinally extended rhombuses this elongation of venous stents is much lower than with transversally extended rhombuses. Due to the great length of venous stents the elongation during compression of the venous stent in the delivery system and during deployment in the blood vessel leads to an undesired significant elongation which is minimized with longitudinally extended rhombuses.

Preferably the longitudinal extension of the rhombuses in unloaded state of the stent is greater than the transversal extension. The longitudinal extension in particular is at least 5%, or at least 10%, or at least 15%, or at least 20%, resp., greater than the transversal extension. The greater the longitudinal extension of the rhombuses relative to the transversal extension is, the lower the relative elongation during compression of the stent.

It is appropriate that the longitudinal extension of the rhombuses in unloaded state of the stent is not greater than the 1.5 fold, or 1.4 fold, or 1.3 fold, resp., of the transversal extension in order to ensure a sufficient compression stability of the stent.

A venous stent made from a braided tubular supporting member can be braided from one or more wires. These wires are braided such that they extend in one or more strands each along the entire length of the stent. One strand thus is a section of one wire which extends from the distal to the proximal end of the stent.

According to another aspect of the present invention a venous stent is characterized in that it is braided with one or more wires such that sections of the wire or the wires, resp., delimit rhombuses, and that each sections of the wires which extend along the entire length of the stent are called strands, whereas the number of strands results from multiplication of the wire diameter $D_d$ with a stent diameter $D_s$ and a factor F. The herefrom resulting calculated value has to be rounded up or down, resp., to an integer. The factor F is a function dependent from the wire diameter $D_d$. The factor F is subject to a tolerance of ±30%. In particular the factor F can be subject to a tolerance of ±20% and preferably to a tolerance of ±10%. The function of the factor F can be described by the following spline functions:

Polynomial 1: (for $0.05 \leq D_d \leq 0.08$)
$F=91.64+44.35\ D_d-20553.34 D_d^2+137022.25 D_d^3$
Polynomial 2: (for $0.08 < D_d \leq 0.1$)
$F=255.59+-6103.93\ D_d+56300.07\ D_d^2-183200.28\ D_d^3$
Polynomial 3: (for $0.1 < D_d \leq 0.12$)
$F=54.05+-90.64\ D_d-3668.35\ D_d^2+16694.46\ D_d^3$
Polynomial 4: (for $0.12 < D_d \leq 0.15$)
$F=113.30+-1576.24\ D_d+8730.26\ D_d^2-17746.13\ D_d^3$
Polynomial 5: (for $0.15 < D_d \leq 0.18$)
$F=38.95+-79.93\ D_d-1276.36\ D_d^2+4490.79\ D_d^3$
Polynomial 6: (for $0.18 < D_d \leq 0.2$)
$F=193.93+-2660.39\ D_d+13052.63\ D_d^2-22044.37\ D_d^3$
Polynomial 7: (for $0.2 < D_d \leq 0.22$)
$F=-114.94+1969.54\ D_d-10089.39\ D_d^2+16525.66\ D_d^3$
Polynomial 8: (for $0.22 < D_d \leq 0.25$)
$F=147.58+-1609.72\ D_d+6178.66\ D_d^2-8122.89\ D_d^3$
Polynomial 9: (for $0.25 < D_d \leq 0.3$)
$F=29.54+-194.24\ D_d+518.94\ D_d^2-576.60\ D_d^3$
Polynomial 10: (for $0.3 < D_d \leq 0.35$)
$F=110.08+-910.08\ D_d+2572.00\ D_d^2-2449.52\ D_d^3$ Preferably the wire is made from nitinol and the wire diameter is about 0.05 mm to 0.35 mm. A stent made from thin wire preferably has more strands than a stent made from thick wires.

According to a preferred embodiment of the venous stents the strands are pairwise inter-connected with each other at least at one end of the stent, whereas this pairwise inter-connection forms a bent section. These bent sections constitute round ends. The round ends ensure that the stent does not incise into the blood vessel. This provides an atraumatic realization.

Preferably the stent is provided with round ends at the proximal as well as at the distal end. The round ends can be formed by bending of a long wire into several strands. The ends of a wire also can be pairwise welded and/or crimped together so that the wire forms an endless loop. The weld seam or the crimp connection can be arranged in the region of the round ends but also in the region of the strands.

The stent may have pairwise twisted strands at at least one end and preferably at both ends. Thereby the strands are pairwise fixed together by which the stability of the stents in the end regions is increased if no round ends are provided.

Loops may be provided at the pairwise twisted ends of the strands which provides a similarly atraumatic ending as the above explained round ends.

The twisted ends of the strands may also be welded so that a tight cohesion is ensured, an atraumatic ending is provided, and, hence, the compression stability in this section of the stent is increased because the strands cannot move anymore one against the other.

The stent may also have a twisted region in which two or more sections of the wire or the wires, resp., are twisted with each other. The twisted region preferably extends over a short section in longitudinal direction of the stent and along the entire circumference of the stent. This twisted region prevents movement of the strands twisted together in axial direction towards each other. Thereby an axial fixation of the strands is achieved. On the other hand the twisted sections are highly flexible in radial direction. Such a twisted region effects an axial decoupling of the sections of the stents which are linked together by the twisted region.

According to a further improvement of the stent it can be provided at one or both ends with a region widened (flared) relative to the other sections of the stent. This widened region serves for local fixation of the stent in the vein.

The widened region preferably extends over a length of at least 5 mm. The widening of the diameter of the stent by the widened region preferably is at least 0.5 mm, in particular at least 1.0 mm, and preferably at least 1.5 mm.

Furthermore, a reinforcement ring can be provided in the widened region. This reinforcement ring can be formed by transversal rhombuses. In this short section the rhombuses thus have a greater transversal extension than longitudinal extension as compared to the other sections of the stent. Hereby the stent in the widened region possesses a higher radial stiffness or compression stability, resp., whereby the reinforcement effect is further supported. As the rhombuses compressed in longitudinal direction are provided only in a short region the increase in elongation of the stent during compression is low.

An alternative reinforcement may be simply achieved by axial squeezing of the stent. After braiding a stent consisting of nitinol wire it is heat treated in the unloaded state by which the material structure in the wire is set so that the stent maintains the "relaxed state" without internal tensions. Hereby the stent radially expands a bit and the rhombuses are compressed in longitudinal direction. The heat treatment of the stent may be executed in several sub-steps, whereby in the first step initially the basic shape of the stent is imprinted so that the braid is stabilized before in subsequent steps the widened section or sections, resp., are structurally fixated by a second heat treatment.

The above explained aspects can be executed independent of each other. Of course it is also possible to provide stents in which several of these independent aspects are jointly combined.

The stents according to the invention may also be positioned across the inguinal ligament without having them breaking which is a significant risk for laser-cut stents. The stents according to the invention possess a high positioning stability, in particular if they comprise widened regions and/or reinforcement sections. The risk of dislocation from the initial deployment position, therefore, is significantly reduced in comparison to known stents. The vena iliaca is intolerant towards lesions remaining after stenting. Concluding, long stents are advantageous. The stents according to the invention can be manufactured in any desired length. Also long stents according to the invention can be provided with atraumatic ends (round ends, loops).

Another aspect of the present invention concerns a system for putting in place a stent made from a braided tubular splinting member and in particular of a stent for splinting a vein. The system comprises an implantation catheter with a chamber for accommodating a stent in its compressed state, a positioning catheter which is located inside the implantation catheter and can attach concisely to the compressed stent, a flexible anchor wire which is threaded through the openings at the proximal end of the stent, a latch wire which extends along the positioning catheter and which is embraced by at least one loop of the anchor wire so that during removal of the latch wire the anchor wire is released and can be pulled out of the stent and the positioning catheter which then leads to deployment of the stent.

During deployment of a stent in a blood vessel the stent initially is located in the implantation catheter in compressed state. The stent in that situation is located in the region of the posterior end of the implantation catheter and is in contact with the inner surface of the implantation catheter. The positioning catheter attaches concisely to the proximal end of the stent and extends across the implantation catheter to the proximal end of the implantation catheter. The anchor wire is hooked into the stent and secured by the latch wire. The anchor wire is led out of the positioning catheter and the implantation catheter. Herewith it is possible to apply a tensile force via the anchor wire to the stent.

Preferably the positioning catheter has at least two and in particular three chambers which extend across its entire longitudinal extension. A first chamber is intended for carrying through the latch wire and/or the anchor wire and the second chamber for carrying through a guidewire. The anchor wire and the latch wire can also be carried through in two separate chambers.

This catheter system is inserted into the vessel of a human or animal body. The catheter system is advanced until the catheter is located at the intended position. Subsequently the implantation catheter is retracted a bit whereby the stent is released. In this situation it is possible to again modify the position of the stent and to again push the implantation catheter over the stent because the stent can be held back by the anchor wire. Herewith for the first time a system for deployment of a braided stent has become available with which a full repositioning—as long as the anchor wire and the latch wire have not been removed—is ensured also in case that the stent has already been fully deployed and expanded. All known systems for deployment of a braided stent allow repositioning of the stent by pulling it back into the system only as long as a significant portion of the stent is still located in compressed state in the system.

Once the stent has been deployed at the intended position the latch wire is retracted. Thereby the anchor wire is released and it can be removed from the stent. The positioning catheter and the implantation catheter are completely pulled out of the vessel.

After the implantation catheter has been pulled back a bit and the anchor wire has been released the latch wire and the anchor wire are fully removed from the vessel to be splinted whereas it is basically irrelevant which of the two wires is removed first. Subsequently the positioning catheter is removed from the implantation catheter and from the vessel to be splinted and lastly the implantation catheter is removed. The guidewire in doing so can be left in position for subsequently carrying out further interventional maneuvers. The guidewire on the other hand may first be removed, before the stent is deployed, if this is desired.

If the anchor wire is removed before the positioning catheter is removed, then it is ensured that the stent will not be retracted a bit together with the anchor wire.

If first the positioning catheter and then the implantation catheter is removed, then only once a catheter is pulled along the inner surface of the vessel to be splinted and less friction is produced at the inner surface of the vessel.

The above explained stent and the system for putting in place a stent have been developed and designed for splinting a vein. This stent, therefore, is optimally adapted to the requirements for splinting a vein. With this stent, however, also other vessels and/or cavities and/or hollow bodies and/or lumen in a human or animal body may be splinted. This applies particularly if the splinting has to be carried out over a longer section than usual for common arterial stents.

Figure 2:
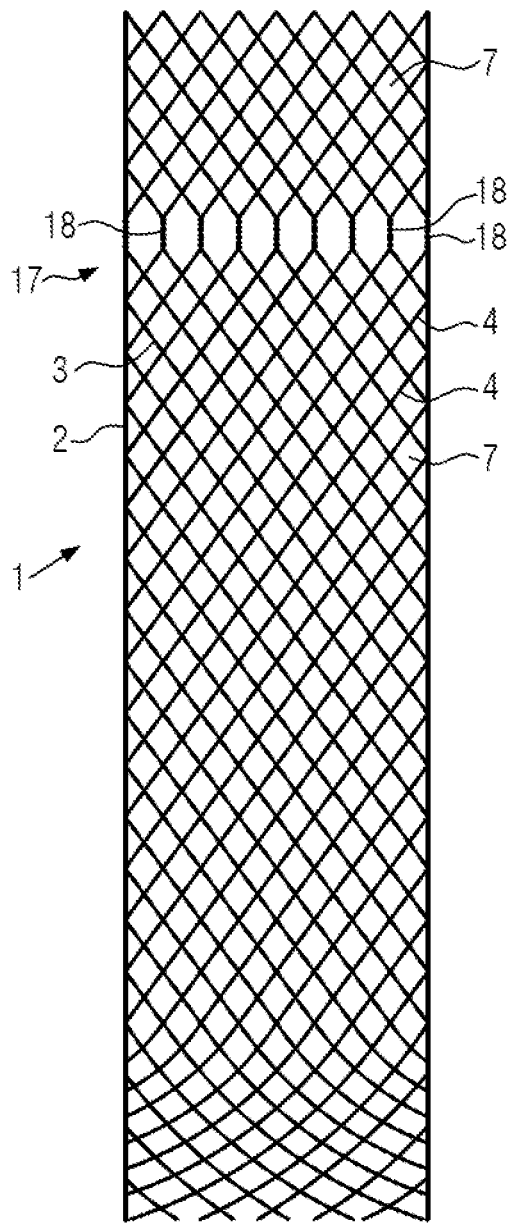
Figure 3A:
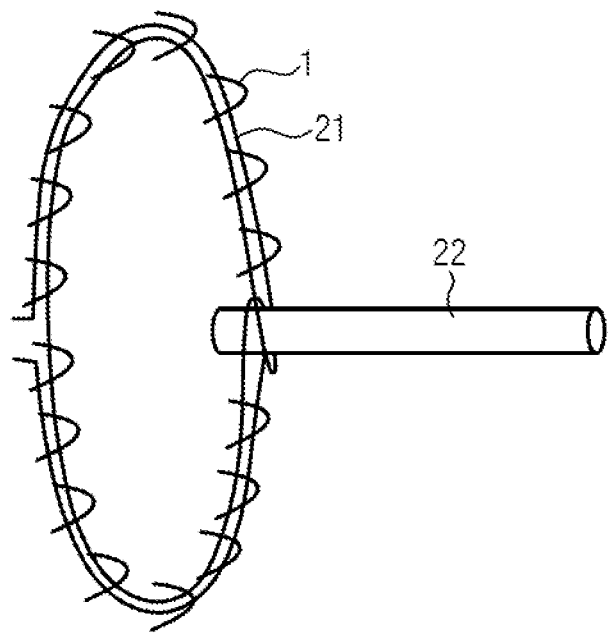
Figure 3B:
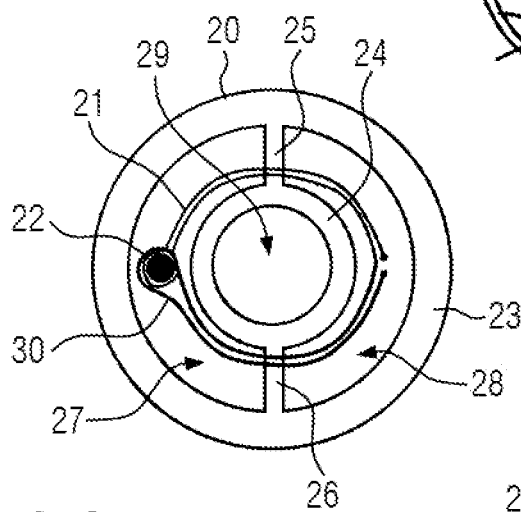
Figure 3C:
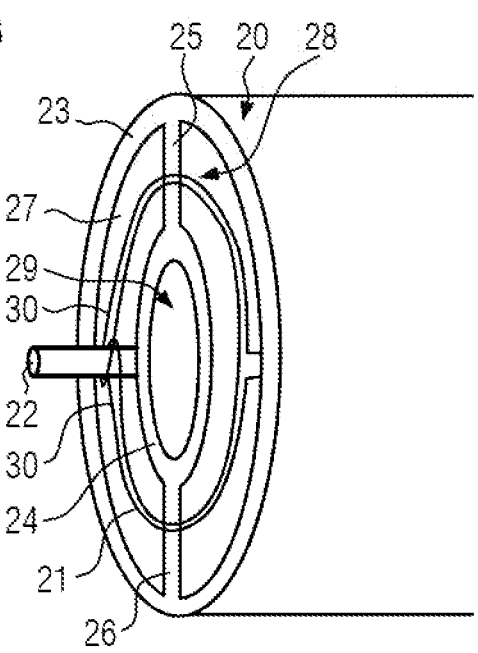
Figure 4:
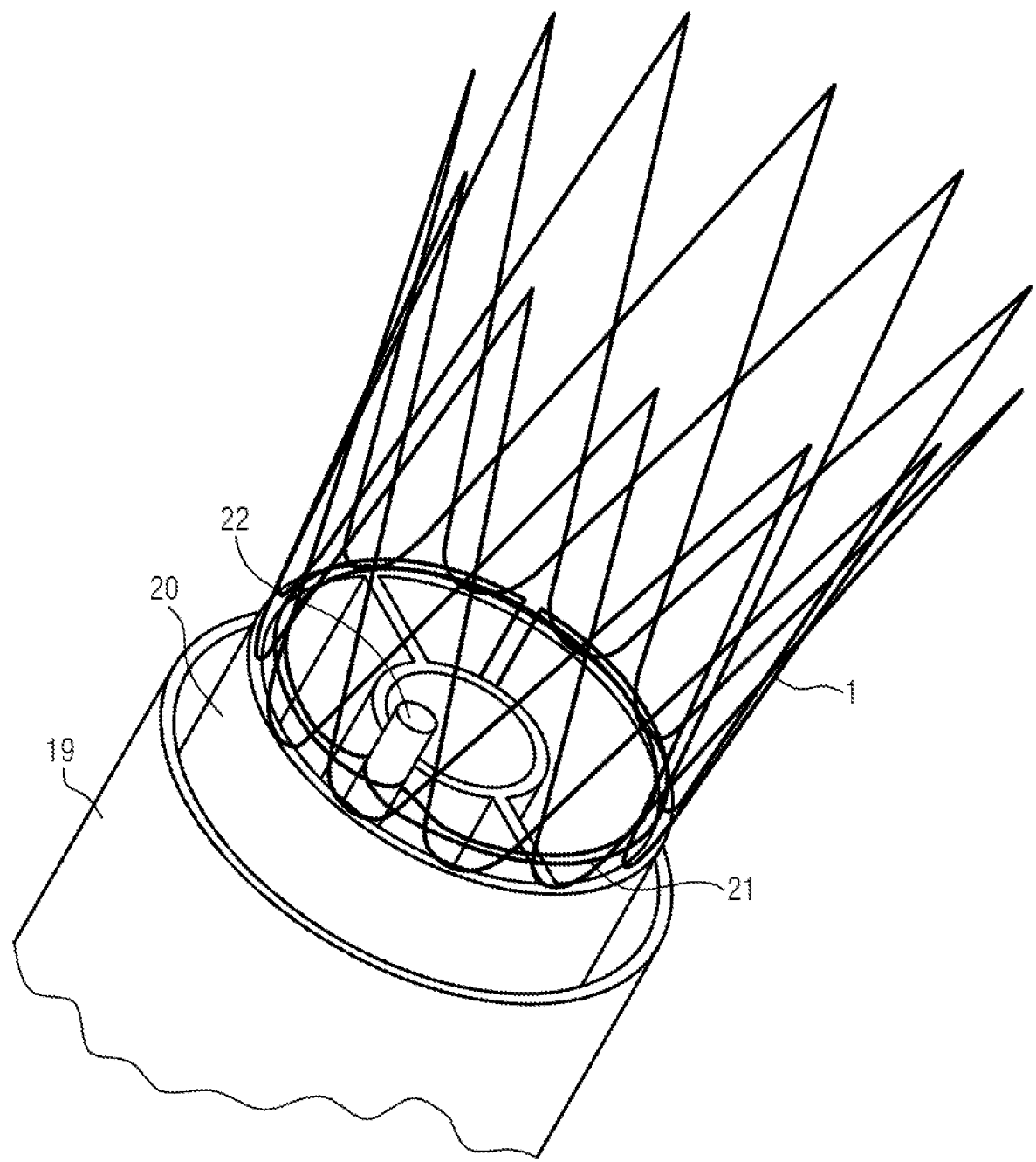
Figure 5:
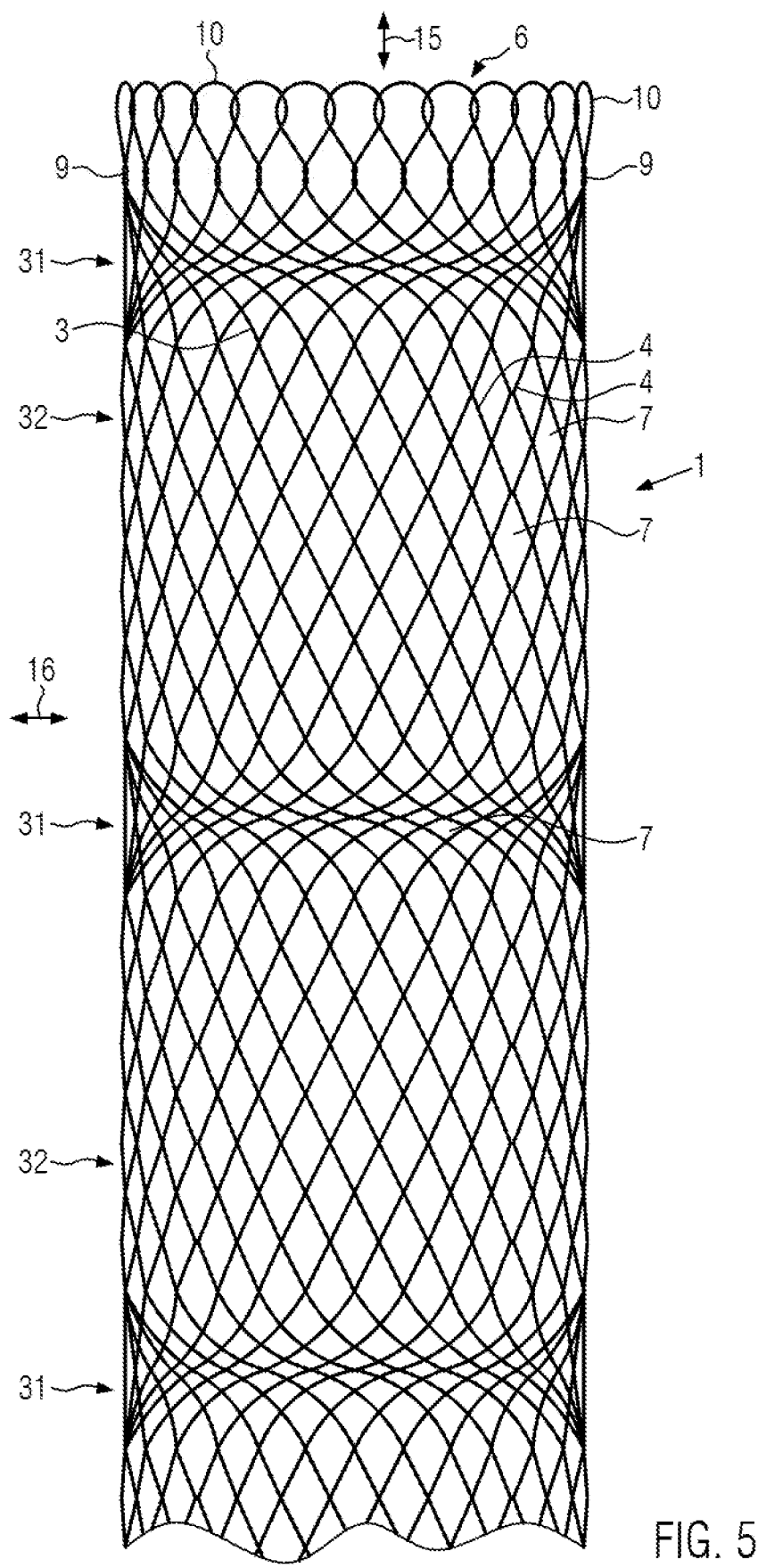
Figure 7:
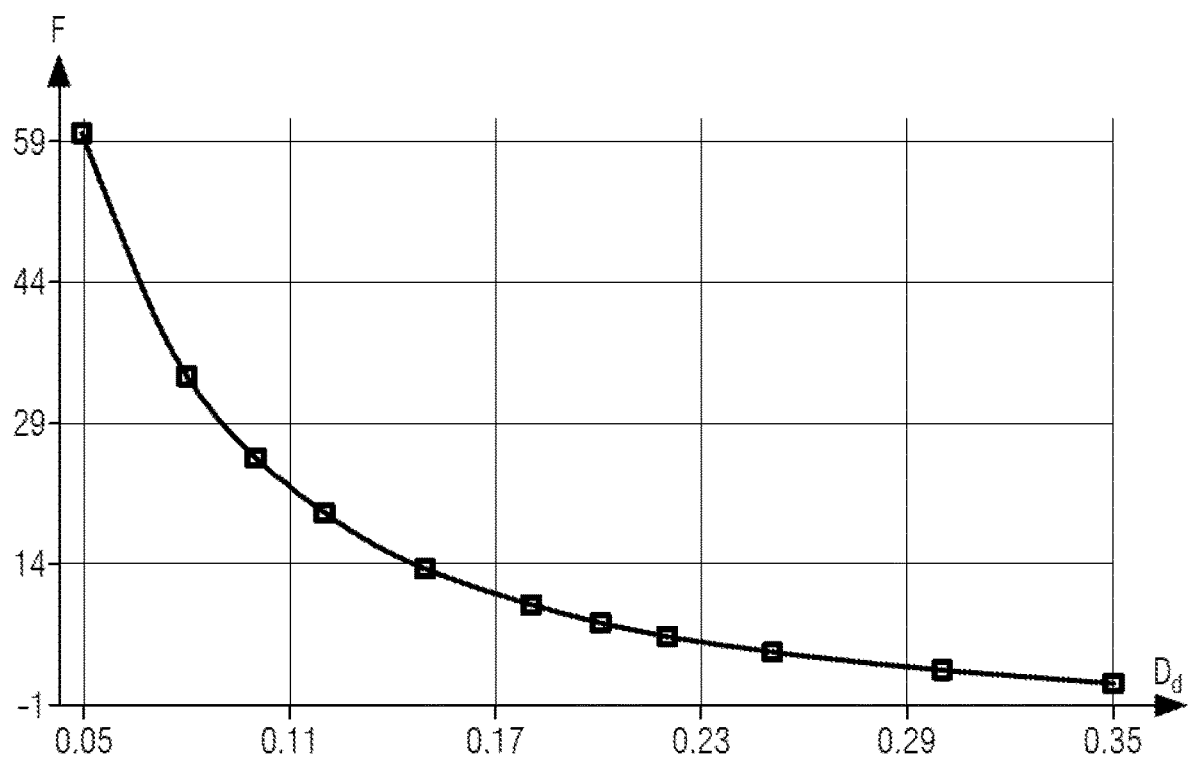
Figure 8:
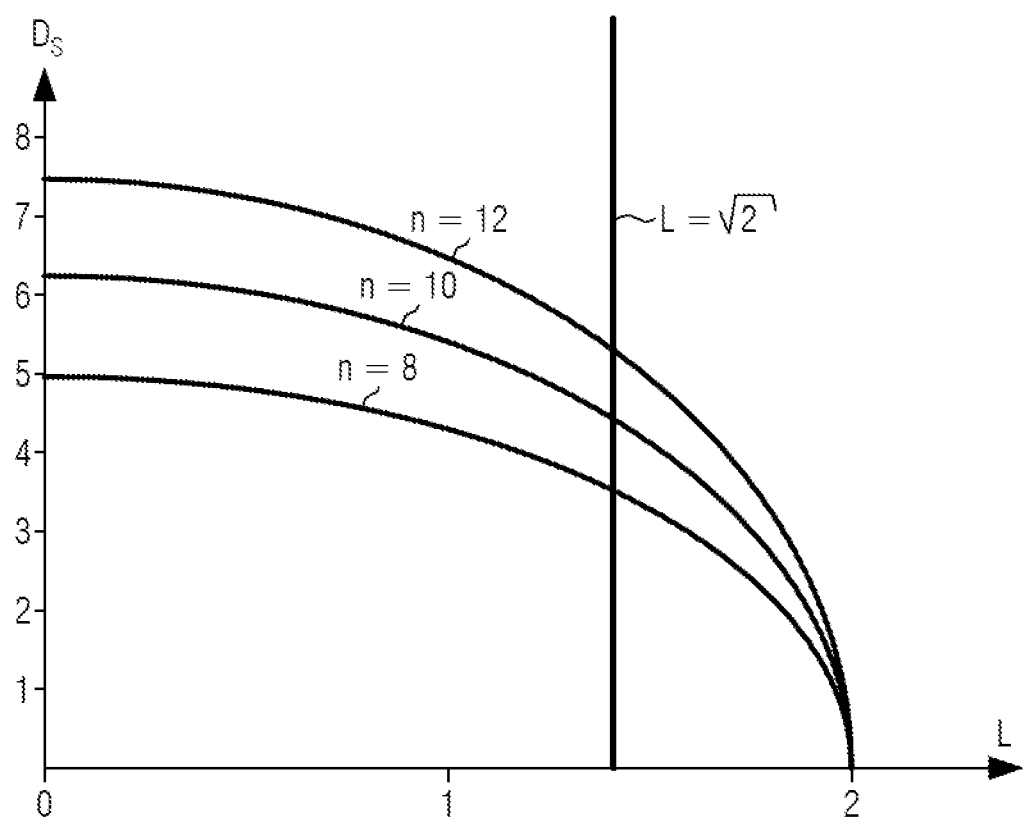

The invention hereinafter is explained in more detail by means of the drawings. The drawings show in:

FIG. 1a a venous stent schematically in a side view,

FIG. 1b an end region of a venous stent with so-called "round ends" schematically in a side view, FIG. 2 another embodiment of a venous stent schematically in a side view, FIGS. 3a-3c schematically a positioning system for a venous stent and for other stents, whereas parts of the stent and of the system are presented in perspective views (FIGS. 3a, 3c) and in a front view (FIG. 3b; without stent), and FIG. 4 the system for putting in place a stent according to FIGS. 3a-3c in a perspective view, FIG. 5 another embodiment of a venous stent schematically in a side view, FIG. 6 a table which comprises essential data of stents with different wire thicknesses and varying numbers of strands, FIG. 7 a diagram of a factor F for calculation of the number of strands of a stent dependent on the wire diameter $D_d$, and FIG. 8 a diagram which displays the diameter of the stent $D_d$ in dependency of the length l of rhombuses of the stent.

A stent 1 has a supporting member 2 for splinting a vein. The stent 1 can exclusively consist of the supporting member 2. Yet, it is also possible that at the supporting member 2 further functional parts, such as e.g. filters or similar, are provided which do not have a supporting function.

The supporting member 2 is braided from one or more wires 3. Each one of the wires 3 forms one or more strands 4, whereas each strand extends from a proximal end 5 of the stent 1 to a distal end 6 of a stent 1. Within the herewith formed braid the respective strands 4 cross each other pairwise, whereby rhombuses 7 are delimited by the strands 4.

Such a braided stent 1 has a significantly higher resiliency and elasticity in comparison to common stents cut from tube sections.

The wires 3 preferably consist of metal, particularly a shape memory metal. The preferred material is nitinol. Generally also other materials such as steel or stiff, in particular fiber-reinforced polymers can be used.

The stent preferably is provided with so-called "round ends" 8 at one end and particularly at both ends (FIG. 1b). The round ends are formed by bending of a wire 3 into several strands 4, whereby the wire in the region of bending has an about circular segment shaped form and is not kinked. The ends of the wires may also be pairwise welded or crimped together so that the wire forms an endless loop. The connection point may be positioned in the region of the round ends 8 but also in the region of the strands 4. By welding or crimping several wire sections can be combined into a single endless wire.

In the embodiment shown in FIG. 1a the stent 1 is formed from 16 wires 3 which each are bent into two strands 4. The stent thereby provides 32 strands 4. At the distal end 6 both strands 4 of each wire 3 are twisted together into a twisted section 9 and each forms a loop 10 with their end-standing wire section.

The loops 10 as well as the round ends 8 provide an atraumatic ending.

At the proximal end 5 the free ends of two strands 4 are twisted together to form another twisted section 11. In the twisted section 11 the strands 4 or the wires 3, resp., can be soldered together.

The twisted sections 9 and 11 pairwise fixate the strands 4 respective to their axial movability. Hereby the stiffness in the end region of the stent 1 is increased.

The stent 1 provides at the proximal end 5 as well as at the distal end 6 each a widened region 12, 13. A main section 14 extending between the widened regions 12, 13 provides in unloaded state an essentially constant diameter. The diameter of the main section 14 in unloaded state typically is 10 to 20 mm. The rhombuses 7 of the main section 14 in longitudinal direction 15 are not shorter than in transversal direction 16 and preferably they are longer in longitudinal direction 15 than in transversal direction 16.

The longitudinal extension of the rhombuses in unloaded state preferably is at least 10% and in particular 20% greater than the transversal extension.

The diameter $D_s$ of the stent is described by the following formula:

$$D_s = \frac{n}{\pi}\sqrt{4-l^2},$$

Wherein n is the number of rhombuses 7 of the stent across the circumferential direction and l the size of the rhombuses in longitudinal direction 15. In this formula the basis are rhombuses with four equally long side edges whereas the length of a side edge is normalized to "1" so that with this formula the diameter $D_s$ is presented with the "length unit of a side edge".

FIG. 8 displays the graphs of this function for n=12, n=10 and n=8, resp. For a length l of the rhombuses of √2 (=1.4142) the length of the rhombus is identical to its height. Then it is a square rhombus. One can detect in these graphs that the change of the length of the rhombus in relation to the change of the diameter of the stent is lower if the rhombuses have a length at least as great as their height.

If the height, however, is greater, then a small changing in the diameter of the stent effects a large change in its length.

A braided stent 1 whose majority of rhombuses is at least as long as high during squeezing is much less elongated than a stent whose majority of rhombuses has a greater transversal extension than longitudinal extension. By this shape of the rhombuses it is ensured that the entire increase in length of the stent is rather small, even if these are in total very long (e.g. at least 10 cm, or at least 20 cm, or at least 30 cm, resp.).

Preferably the longitudinal extension of the rhombuses 7 of the main section 14 in unloaded state is not greater than the 1.5 fold of the transversal extension, and preferably not greater than the 1.4 fold, or the 1.3 fold, resp., of the transversal extension. Herewith it is ensured that the stent provides sufficient compression stability. The compression stability amongst others is determined by the rhombus shape, wherein stents with highly longitudinally elongated rhombuses provide a significantly lower compression stability than stents with less elongated rhombuses. The compression stability, however, is also determined by additional parameters, in particular the number of strands and the thickness of the wire used.

The widened regions 12, 13 can be produced amongst other means by squeezing of the respective section of the stent. Hereby the rhombuses are squeezed a bit in longitudinal direction 15 and elongated a bit in transversal direction 16. This leads to that the diameter of the stent 1 is increased in the widened regions 12, 13 as compared to the main section 14. In addition the widened regions 12, 13 provide a higher compression stability than the main section 14, due to their rhombuses 7 being more elongated in transversal direction. Such a stent is preferably manufactured from a shape memory metal, whereas the stent is fixated in its shape after braiding with a first heat treatment, wherein the stent 1 is held with a constant diameter over its entire length which corresponds to the diameter of the stent in the region of the main section 14. By this heat treatment the material structure in the wire is set so that the stent maintains the "relaxed state" without internal tensions. Subsequently the end regions of the stent are squeezed a bit so that the widened regions 12, 13 are formed. In this condition the stent is heat treated for a second time so that the widened sections 12, 13 are relaxed and maintain this shape. Due to the greater transversal expansion of the rhombuses in the widened region 12, 13 here a greater relative longitudinal extension than in the main section 14 is caused during compression of the stent. As these widened regions 12, 13 in comparison to the other parts of the stent are very short (e.g. 5 mm to 3 cm) the elongation caused by them is low and can be neglected.

Due to the rhombuses 7 more elongated in transversal direction 16 the widened regions 12, 13 provide a high radial stability.

The widened regions 12, 13 serve for fixation of the position of the stent in the body vessel, in particular in a vein.

The stent may also be provided with a decoupling section 17 in which each two strands 4 are twisted together to further twisted sections 18 (FIG. 2). This decoupling section 17 decouples the two braided sections neighboring the decoupling section 17 in radial direction so that the two braided sections can be provided with different diameters without causing tensions in the stent. The twisted sections 18 can proceed to radial outside or to radial inside without hereby tensions or at least no significant tensions are caused. Another effect of this decoupling section 17 is that the strands 4 are pairwise fixated in longitudinal direction 15. Hereby a relative movement of the strands 4 in longitudinal direction is prevented.

A stent 1 may be provided with no, one or more such decoupling sections 17.

The stent 1 can be provided with varying diameters (10 mm-20 mm) with varying wire thicknesses (0.05 mm-0.35 mm). Dependent from the wire strength or wire thickness, resp., and the diameter of the respective stent the stent has to be designed with a varying number of strands 4. The table shown in FIG. 6 comprises the data for the wire diameter $D_d$, the stent diameter $D_s$, and a factor F for calculation of the number of strands of a stent. The stent has the same number of strands with the other slope in order to delimit one rhombus 7 by each two pairs of strands with differing slope. The number of strands n results from multiplication of the wire diameter $D_d$ with the stent diameter $D_s$ and the factor F. The resulting calculated value has to be rounded up or down, resp., to an integer. The factor F is a function dependent from the wire diameter $D_d$. In the table ranges with the respective suitable number of strands n are provided. The actually suitable number of strands varies by about ±2 strands around the calculated value. In the present example of an embodiment each one of the wires 3 forms two strands 4. Therefore, all stents 1 have an even number of strands.

The more strands that are provided, the higher the compression stability of the stent is. However, there are other influences on the compression stability of the stent such as e.g. the shape of the rhombuses and the actually used material of the wires. The data shown in FIG. 6 apply for nitinol wires.

The factor F dependent from the wire diameter $D_d$ can be described by the following spline functions:

Polynomial 1: (for $0.05 \leq D_d \leq 0.08$)
$F=91.64+44.35\ D_d-20553.34D_d^2+137022.25D_d^3$
Polynomial 2: (for $0.08<D_d \leq 0.1$)
$F=255.59+-6103.93\ D_d+56300.07\ D_d^2-183200.28\ D_d^3$
Polynomial 3: (for $0.1<D_d \leq 0.12$)
$F=54.05+-90.64\ D_d-3668.35\ D_d^2+16694.46\ D_d^3$
Polynomial 4: (for $0.12<D_d \leq 0.15$)
$F=113.30+-1576.24\ D_d+8730.26\ D_d^2-17746.13\ D_d^3$
Polynomial 5: (for $0.15<D_d \leq 0.18$)
$F=38.95+-79.93\ D_d-1276.36\ D_d^2+4490.79\ D_d^3$
Polynomial 6: (for $0.18<D_d \leq 0.2$)
$F=193.93+-2660.39\ D_d+13052.63\ D_d^2-22044.37\ D_d^3$
Polynomial 7: (for $0.2<D_d \leq 0.22$)
$F=-114.94+1969.54\ D_d-10089.39\ D_d^2+16525.66\ D_d^3$
Polynomial 8: (for $0.22<D_d \leq 0.25$)
$F=147.58+-1609.72\ D_d+6178.66\ D_d^2-8122.89\ D_d^3$
Polynomial 9: (for $0.25<D_d \leq 0.3$)
$F=29.54+-194.24\ D_d+518.94\ D_d^2-576.60\ D_d^3$
Polynomial 10: (for $0.3<D_d \leq 0.35$)
$F=110.08+-910.08\ D_d+2572.00\ D_d^2-2449.52\ D_d^3$ The individual polynomials 1-10 of the spline functions are also valid separately from each other. The spline functions describe the relationship (see FIG. 7) between the wire thicknesses $D_d$ and the factors F such as they are presented in FIG. 6.

The constant F is an empirical value which results from a multitude of trials. Appropriate stents can also be provided with a tolerance of the factor F of ±30%, in particular ±20%, and preferably only ±10% or ±5%, resp. Such stents are optimized in respect of their elongation properties and compression stability. The longitudinal extension in the main section 14 of the stent in unloaded state is at least as great as the transversal extension of the rhombuses. Preferably the longitudinal extension of the rhombuses 7 in the main section 14 is greater than the transversal extension but not greater than the 1.5 fold of the transversal extension. This stent preferably is provided with the widened regions 12, 13 which enable a good fixation of the stents in the vessel.

Another embodiment of a venous stent according to the invention provides one or more reinforcement sections 31. Within a reinforcement section the rhombuses 7 in longitudinal direction are shorter than the rhombuses of the other sections of the stent 1. Hereby the other sections are more flexible than the reinforcement sections. These other sections hereinafter are called hinge sections 32.

The rhombuses 7 of the reinforcement sections 31 may, but must not be longer in transversal direction 16 than the rhombuses of the hinge regions 32.

The reinforcement sections 31 can be provided with the same diameter as the hinge sections 32. In this case the strands 4 are braided with a greater braiding angle in the region of the reinforcement sections 31 relative to the longitudinal extension or longitudinal direction 15 of the stent 1 than in the hinge regions during manufacturing of the stent. The reinforcement sections 31 can, on the other hand, also have a greater diameter than the other sections of the stent 1. In that case the reinforcement sections 31 can be manufactured, equal to the above described widened sections, by squeezing or compression of the respective sections in longitudinal direction. At the distal and proximal ends 5, 6 of the stent 1 round ends 8, twisted sections 9 and/or loops 10 with or without twisted sections may be provided, just as in the embodiments displayed in FIGS. 1a and 1b.

The reinforcement sections provide to the stent a high radial stiffness. The hinge sections arranged between the reinforcement sections and whose rhombuses have a greater longitudinal extension than the rhombuses of the reinforcement sections 31, however, are softer and more flexible. Preferably reinforcement sections 31 and hinge sections 32 are provided consecutively alternating. The hinge sections 32 typically are double to tenfold as long as the reinforcement sections 32. The alternating arrangement of reinforcement sections 31 and hinge sections 32 thereby forms a type of link chain made from stiff, ring-type reinforcement sections 31 and the more bendable hinge sections 32. Such a venous stent 1 can adapt to any desired curves of the vein. The reinforcement sections 31 prevent that the vein may collapse and limit the elongation of the hinge sections.

As the stent is braided with continuous strands which extend from the distal end to the proximal end 6 it possesses a homogeneous braid structure. The stent thereby provides a high tear resistance in axial direction which is significantly higher than for comparable stents which are laser-cut from a tube.

For such a venous stent with reinforcement sections 31 and hinge sections 32 the data for determination of the number n of the strands 4 listed in FIG. 6 also apply.

The reinforcement sections 31 exhibit a higher density of strands 4 than the hinge sections 32. In the reinforcement sections 31 the strands 4 are braided with a higher slope relative to the longitudinal extension of the stent 1.

Hereinafter the system for putting in place of a stent will be explained.

This system comprises an implantation catheter 19, a positioning catheter 20, a flexible anchor wire 21 and a latch wire 22. The positioning catheter 20 is arranged movable in the implantation catheter 19 whereby the outer surface of the positioning catheter 20 is in contact with the inner surface of the implantation catheter 19, whereas a sufficient gap is provided therebetween in order to be able to move the positioning catheter 20 within the implantation catheter 19. The implantation catheter 19 has a cylindrical shape. The positioning catheter 20 has a cylindrical outer wall 23 and a concentrically arranged cylindrical inner wall 24, whereas the outer wall 23 and the inner wall 24 are connected with two preferably diametrically opposed arranged ligaments 25, 26. In the region of the inner wall and the outer wall 23 thereby two chambers 27, 28 are provided. The inner wall 24 delimits another chamber or lumen 29 with a circular cross-section. The anchor wire 21 is threaded through the first of the outer chambers 27 and extends through the loops or the openings of the braid, resp., in the proximal end region of the stent 1, and is threaded from the stent 1 inwards to the latch wire 22 by loops 30 positioned at the end. The latch wire 22 is embraced by the loops 30 of the anchor wire 21. The latch wire extends across the second outer chamber 28. The latch wire 22 as well as the anchor wire 21 extend to the outside of the positioning catheter and the implantation catheter 19 and can be handled by an operator. By pulling the anchor wire 21 a tensile force can be applied to the stent 1 pulling in proximal direction of the stent 1. Herewith during a rearward movement it can be ensured that the stent 1 attaches concisely with its proximal end 5 at the positioning catheter 20. Once the latch wire 22 is pulled out of the loops 30 of the anchor wire 21 the anchor wire with its loops is free and can be pulled out of the loops or openings, resp., of the stent 1. Hereby the connection between the anchor wire 21 and the stent 1 can be disengaged and the stent 1 be deployed. Also two or more anchor wires can be provided.

During putting in place of the stent 1 in a blood vessel the stent 1 initially is located in compressed state in the implantation catheter 19. The stent 1 in that situation is arranged in the region of the distal end of the implantation catheter 19 and attaches to the inner surface of the implantation catheter 19. The positioning catheter 20 attaches concisely to the proximal end of the stent 1 and extends across the implantation catheter 19 to the proximal end of the implantation catheter 19.

The anchor wire 21 in the region of the loops 30 is secured via the latch wire 22. The anchor wire 21 and the latch wire 22 are led out of the positioning catheter 20 and the implantation catheter 21 at their proximal ends. This unit, consisting of the implantation catheter 19, the positioning catheter 20, the anchor wire 21, the latch wire 22 and the stent 1 is inserted into the blood vessel until it is positioned at the intended place.

The inner chamber or lumen 29 of the positioning catheter 20 serves for accommodating the guidewire (not shown) which initially is inserted until reaching the desired position in the blood vessel and for guiding this catheter arrangement during insertion into the blood vessel. By providing separate chambers 27, 28, 29 the guidewire, the anchor wire 21 and the latch wire 22 can be threaded separately from each other through the positioning catheter 20.

Once the catheter arrangement is inserted so far into the blood vessel that the stent is located at the desired position then first the guidewire can be removed. Subsequently the implantation catheter 19 is retracted a bit whereas the positioning catheter 20 maintains its position. Thereby it is ensured that the stent 1 is not retracted together with the implantation catheter 19 as it attaches to the front side of the positioning catheter 20. The stent 1 is released from the implantation catheter 19. After deployment of the stent 1 preferably the position of the stent 1 is examined. If it is correct then the latch wire 22 is retracted and the locking of the anchor wire 21 is released. Then the anchor wire can be released from the stent 1 whereby the stent is fully released. Should the position of the stent 1 not be correct then it is possible to push the implantation catheter 19 back over the stent, as long as the anchor wire 21 is locked, and to reposition the stent 1.

Through the lumen 29 also a balloon catheter can be advanced in order to particularly expand sections of the stent 1. This may be especially useful for the widened regions 12, 13 at the ends which are pressed back into the vessels by a locally limited dilation, in order to immobilize the stent in this way.

If the stent 1 is put in place correctly then first the anchor wire 21, the latch wire 22, and the positioning catheter 20 are fully retracted from the blood vessel. Lastly the implantation catheter 19 is pulled out.

LIST OF REFERENCE NUMBERS

1 Stent
2 Supporting body
3 Wire
4 Strand
5 Proximal end
6 Distal end
7 Rhombus
8 Round end
9 Twisted section
10 Loop
11 Twisted section
12 Widened region
13 Widened region
14 Main section
15 Longitudinal direction
16 Transversal direction
17 Decoupling section
18 Twisted section
19 Implantation catheter
20 Positioning catheter
21 Anchor wire
22 Latch wire
23 Outer wall
24 Inner wall
25 Ligament
26 Ligament
27 First chamber
28 Second chamber
29 Chamber/Lumen
30 Loop
31 Reinforcement section
32 Hinge section

The invention claimed is:

1. A system for putting in place a stent, wherein the stent is formed from a braided tubular supporting member, the system comprising:

the stent for splinting a vessel, a latch wire, an anchor wire, an implantation catheter with a lumen for accommodating the stent in a compressed state, a positioning catheter which is located inside the implantation catheter and only a front side of the positioning catheter is attached to the compressed stent ensuring that the stent is not retracted with the implantation catheter, wherein the front side extends perpendicular to a longitudinal axis of the positioning catheter, wherein the positioning catheter provides at least two chambers extending across the entire length of the positioning catheter which are provided for accommodating a guidewire and for accommodating the latch wire and/or the anchor wire, the anchor wire which is flexible and threaded through openings of the stent, wherein the openings of the stent through which the anchor wire is threaded are arranged only at a proximal end region of the stent, the latch wire which extends across one of the chambers of the positioning catheter and is embraced by at least one loop of the anchor wire so that during removal of the latch wire, the anchor wire is released and can be pulled out of the stent and the positioning catheter, wherein the latch wire releases the stent.

2. A method for putting in place a stent, comprising the following steps:

insertion into a vessel or a cavity to be splinted in a human or animal body, of a distal end of a system for placing the stent in a vein, in which the stent is formed from a braided tubular supporting member, the system comprising an implantation catheter with a lumen for accommodating the stent in a compressed state, a positioning catheter which is located inside the implantation catheter and only a front side of the positioning catheter is attached to the compressed stent ensuring that the stent is not retracted with the implantation catheter, wherein the front side extends perpendicular to a longitudinal axis of the positioning catheter, wherein the positioning catheter has at least two chambers extending across the entire length of the positioning catheter which are provided for accommodating a guidewire and for accommodating a latch wire and/or an anchor wire, respectively, the anchor wire which is flexible and threaded through openings of the stent, wherein the openings of the stent through which the anchor wire is threaded are arranged only at a proximal end region of the stent, the latch wire which extends across one of the chambers of the positioning catheter and is embraced by at least one loop of the anchor wire so that during removal of the latch wire, the anchor wire is released and can be pulled out of the stent and the positioning catheter, wherein the latch wire releases the stent, retraction of the implantation catheter, releasing the stent, retraction of the latch wire, releasing the anchor wire, pulling out the anchor wire, the positioning catheter, and the implantation catheter of the vessel or cavity to be splinted.

* * * * *